United States Patent [19]
Wear et al.

[11] Patent Number: 5,874,584
[45] Date of Patent: Feb. 23, 1999

[54] ION-SENSITIVE COMPOUNDS

[75] Inventors: Trevor John Wear, South Harrow; Christopher Peter Moore; Alistair J. Goulden, both of Harrow; Paul D. Beer; Nicholas C. Fletcher, both of South Parks Road, all of England

[73] Assignee: Eastman Kodak Company, Rochester, N.Y.

[21] Appl. No.: 964,815

[22] Filed: Nov. 5, 1997

Related U.S. Application Data

[60] Division of Ser. No. 734,938, Oct. 12, 1996, Pat. No. 5,760,231, which is a continuation-in-part of Ser. No. 356,182, Dec. 19, 1994, abandoned.

[30] Foreign Application Priority Data

Apr. 21, 1993 [GB] United Kingdom .............. 9308214

[51] Int. Cl.$^6$ .................................................. C07D 401/12
[52] U.S. Cl. ............................................................ 546/265
[58] Field of Search ............................................. 546/265

[56] References Cited

U.S. PATENT DOCUMENTS 5,043,415  8/1991  Harris et al. ........................... 528/205

FOREIGN PATENT DOCUMENTS 309291  3/1989  European Pat. Off. .

OTHER PUBLICATIONS

Shinkai, J. Org. Chem, 57, 1516, 1962.

Shinkai, Chem. Letters, 835, 1990.

Pappalardo, Tet. Letters, 32, 7747, 1991.

Shinkai, Bull. Chem. Soc. Japan, 62, 4055, 1989.

Beer, Tetrahedron, 49, 9917, 1992.

*Primary Examiner*—Richard L. Raymond
*Attorney, Agent, or Firm*—John R. Everett

[57] ABSTRACT

An ion-sensitive calix(4)arene compound having the formula $A^{2+}B^{2-}$ wherein A represents a cation capable of forming a receptor-substrate complex with an anion, and B represents sulfate, nitrate or borate, characterized in that the cation is an anion receptor represented by the formula

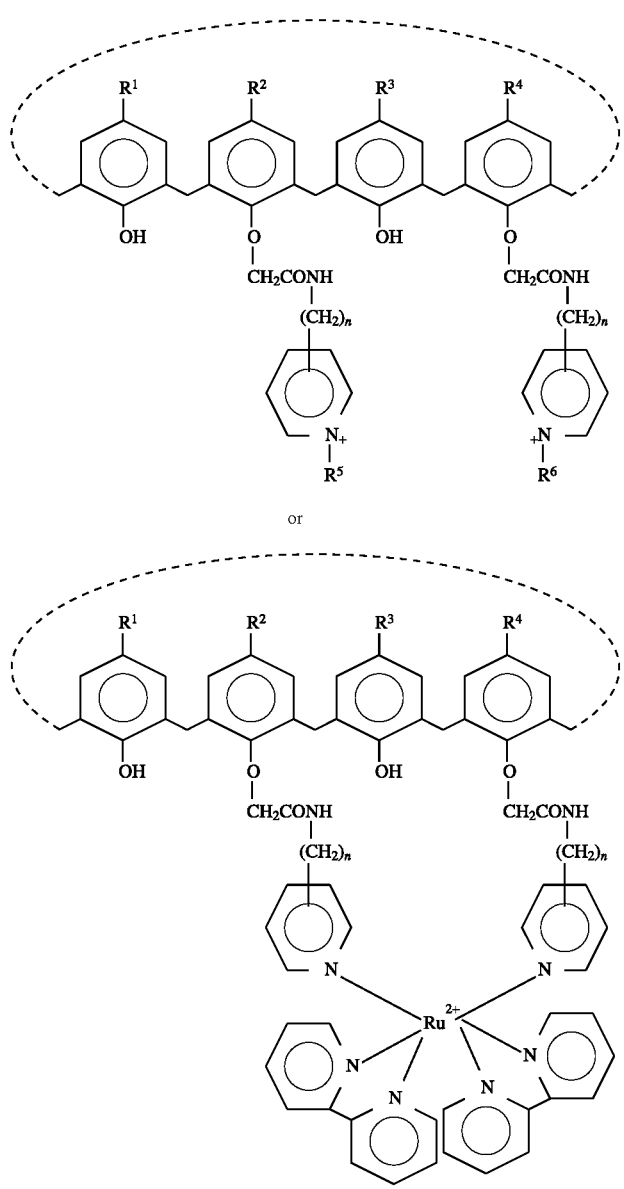

wherein
  $R^1$, $R^2$, $R^3$ and $R^4$ are each independently a substituted or unsubstituted alkyl group or a substituted or unsubstituted aryl group wherein substituents are selected from alkyl C(O)NH—, aryl C(O)NH—, alkoxy, aryloxy, alkoxycarbonyl, aryloxycarbonyl, alkylsulfonamido, arylsulfonamido, alkylcarbonyl, alkoxycarbonyl, aryloxycarbonyl, cyano and nitro;
  $R^5$ and $R^6$ are each independently H or a lower alkyl group having from 1 to 4 carbon atoms, or $R^3$ and $R^4$ taken together represent an ethylene bridging group; and, n is 0 or 1.

5 Claims, 2 Drawing Sheets

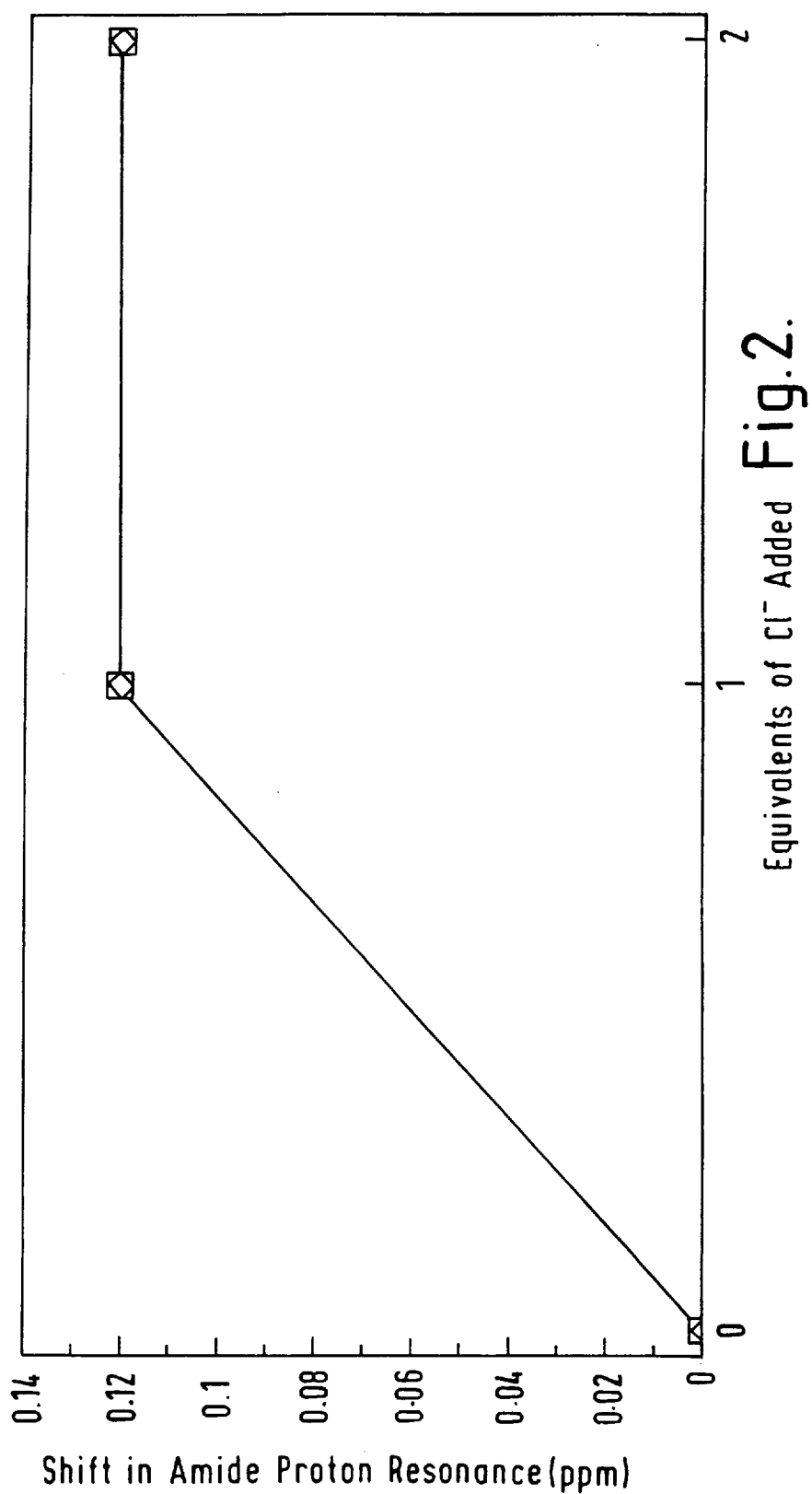

ION-SENSITIVE COMPOUNDS

This application is a division of application Ser. No. 08/734,938, filed Oct. 12, 1996, now U.S. Pat. No. 5,760,231, which is a continuation-in-part of application Ser. No. 08/356,182, filed Dec. 19, 1994, entitled Ion-Sensitive Compounds, by Trevor Wear et al, now abandoned.

FIELD OF THE INVENTION

The invention relates to ion-sensitive compounds. More particularly, the invention relates to ion-sensitive compounds comprising a receptor designed to bind anionic species by the formation of a receptor-substrate complex.

BACKGROUND OF THE INVENTION

Anion receptors comprising a plurality of quaternary amine groups are known. Examples of such compounds may be seen in P. G. Potvin and J-M Lehn, *Prog. Macrocyclic Chem.*, 1987, 3, 214.

L. A. Summers, "The Bipyridinium Herbicides", Academic Press, New York, 1980, describes the use of certain compounds comprising diquaternary 2,2'-bipyridinium moieties in herbicidal applications.

Metal ion centers have also been utilized in systems for the recognition of anions as described in D. N. Reinhoudt, *J. Am. Chem. Soc.* 1992, 114, 9671–9673.

PROBLEM TO BE SOLVED BY THE INVENTION

There is a continuing need to provide new receptor compounds for a variety of applications. For example, there is a need for compounds which can be incorporated in electrochemical or optical sensors for anion determination. There is also a need for compounds which can be used in removal devices where levels of a given anion need to be kept low.

It is also desirable to provide receptor compounds which can be readily synthesized.

SUMMARY OF THE INVENTION

The ion-sensitive calix(4)arene compound having the formula $A^{2+}B^{2-}$ wherein A represents a cation capable of forming a receptor-substrate complex with an anion, and B represents sulfate, nitrate or borate, characterized in that the cation is an anion receptor represented by the formula

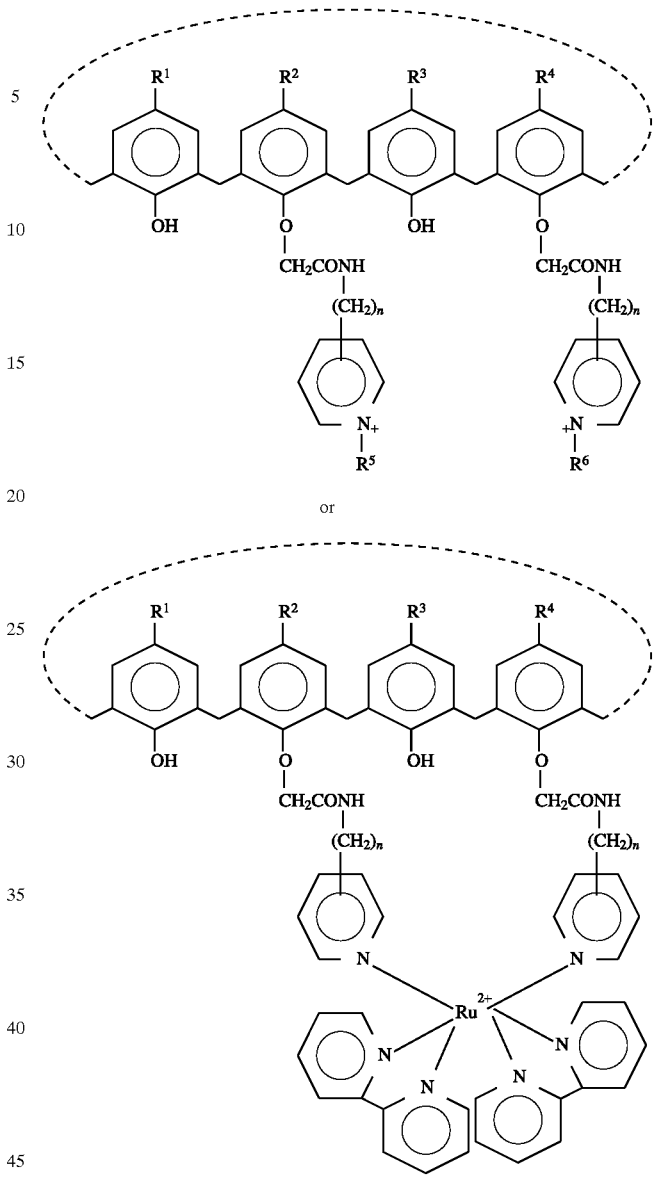

wherein $R^1$, $R^2$, $R^3$ and $R^4$ are each independently a substituted or unsubstituted alkyl group or a substituted or unsubstituted aryl group wherein substituents are selected from alkyl C(O)NH—, aryl C(O)NH—, alkoxy, aryloxy, alkoxycarbonyl, aryloxycarbonyl, alkylsulfonamido, arylsulfonamido, alkylcarbonyl, alkoxycarbonyl, aryloxycarbonyl, cyano and nitro;

$R^5$ and $R^6$ are each independently H or a lower alkyl group having from 1 to 4 carbon atoms, or $R^3$ and $R^4$ taken together represent an ethylene bridging group; and, n is 0 or 1.

The invention also provides a method of sensing an anion in solution by contacting the anion with a compound comprising a cation which is a receptor for the anion to form a receptor-substrate complex and sensing a detectable change which results from the formation of the complex characterized in that the compound is a compound of the invention.

ADVANTAGEOUS EFFECT OF THE INVENTION

The compounds of the invention show selectivity to anions and are useful for the electrochemical and/or optical detection of anions, especially halides and particularly chlorides.

BRIEF DESCRIPTION OF THE DRAWINGS

FIG. 2 is a graphical representation of the observed $^1$H NMR response of the compound of Example 2 on addition of a chloride ion source.

DETAILED DESCRIPTION OF THE INVENTION

Figure 1:
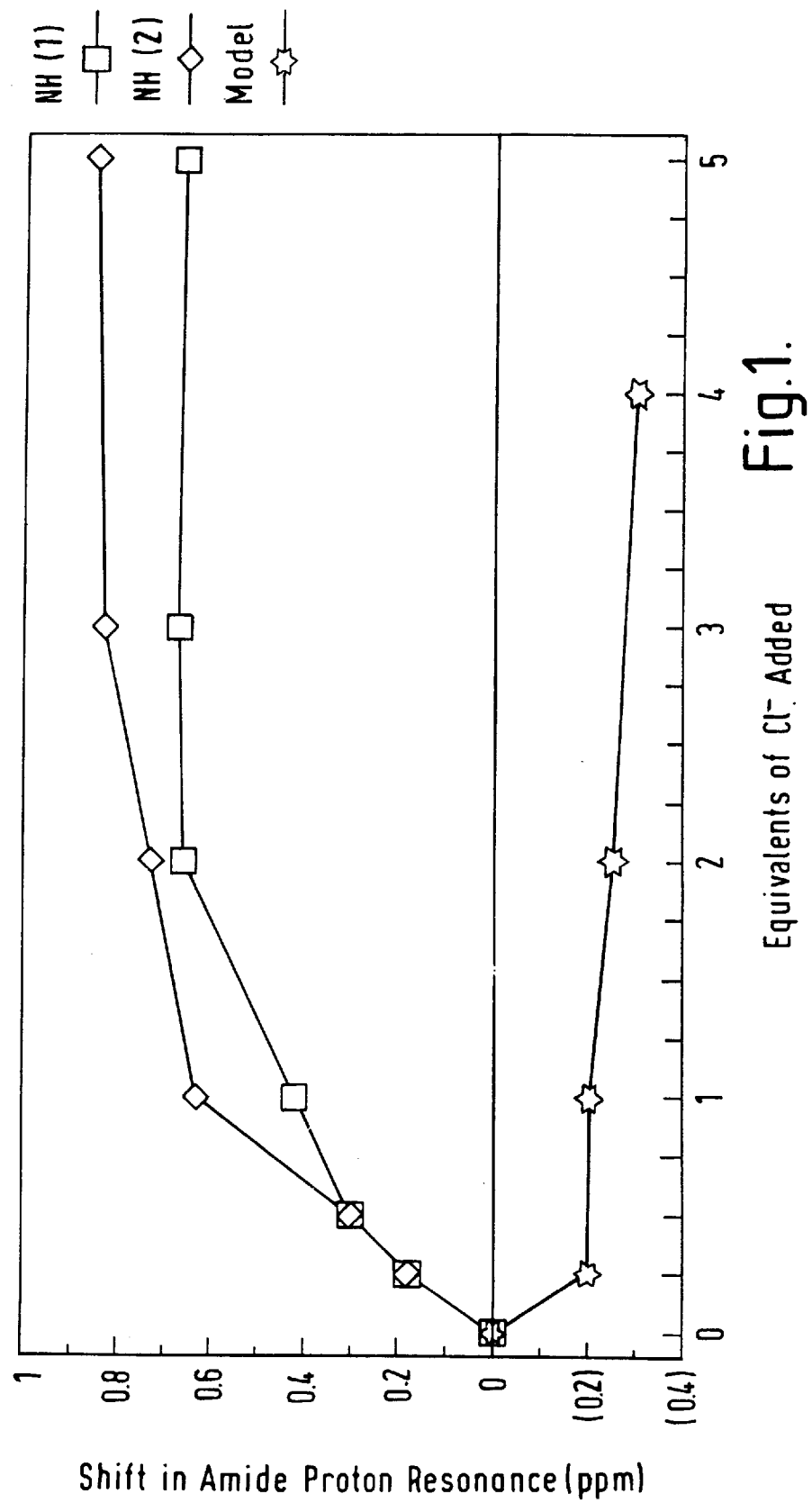
FIG. 1 is a graphical representation of the observed $^1$H NMR response of the compound of Example 1 on addition of a chloride ion source.

Preferably, $R^1$, $R^2$, $R^3$ and $R^4$ are each independently H, a substituted or unsubstituted alkyl group having from 1 to 20 carbon atoms e.g. methyl, ethyl, propyl, butyl, pentyl, hexyl and eicosyl. Tertiary alkyl groups are particularly preferred e.g. t-butyl. Suitable substituents include alkylamido, arylamido, alkoxycarbonyl, aryloxycarbonyl, alkylsulfonamido, arylsulfonamido, alkylcarbonyl, alkoxy, cyano and nitro.

Preferably, $R^1$, $R^2$, $R^3$ and $R^4$ are each independently a substituted or unsubstituted phenyl group. Suitable substituents include alkyloxy, aryloxy, alkyl C(O)NH—, aryl C(O)NH—, alkylsulfonamido, arylsulfonamido, alkyloxycarbonyl, aryloxycarbonyl and nitro.

Preferably, $R^5$ and $R^6$ are each methyl groups.

The synthesis of unsubstituted and substituted calixarenes is well documented. By way of example, reference is made to Calixarenes by C. David Gutsche, Royal Society of Chemistry, 1989.

Compounds of the invention can be prepared via the condensation reaction of the 1,3 diacid chloride of an unsubstituted or 4-substituted calix arene and two moles of 4-aminopyridine or 4-aminomethylpyridine. Quaternization of the pyridine nitrogen atoms of the resulting dipyridyl derivative provides compounds having the structure I. Alternatively, reaction of the resulting dipyridyl derivative with ruthenium dipyridyl dichloride dihydrate provides compounds having the structure II.

The compounds of the invention can be used in a method of sensing anions as indicated above. The detectable change resulting from formation of the complex can be measured by any suitable means such as NMR measurement, electrochemical measurement e.g. cyclic voltammetry, or optical measurement e.g. fluorescence spectroscopy.

Specific examples of the preparation of compounds of the invention are given as follows.

EXAMPLE 1

1,3 Diester

The p-tert-butylcalix arene used was recrystalized from hot toluene/ethanol and dried under vacuum. Acetone was dried by standing over calcium sulphate overnight then distilled from fresh calcium sulphate.

A slurry of p-tert-butylcalix arene (6.00 g, 8.10 mmol) and anhydrous potassium carbonate (2.24 g, 16.2 mmol) were stirred in dry acetone (200 ml) at room temperature for 10 mins. Bromoethylacetate (1.81 ml, 16.2 mmol) was added and the reactants stirred for 18 hours at room temperature. Salt precipitated was removed by filtration and acetone removed to leave the crude product. This was taken up in dichloromethane, washed with water to leave the desired product as a white powder. No further purification was required. Yield 100%.

1,3 Diacid

Diester (5.24 g, 6.4 mmol) was taken up in approximately 1.5 l of warm ethanol before 80 ml sodium hydroxide was added and the solution refluxed for 12 hours. The ethanol was removed to leave a white solid which was dried under vacuum. Water was added to this solid to form a brown slurry which was acidified to pH1 using concentrated hydrochloric acid. A color change was noted during acidification from brown to cream and then the organic components of this slurry were extracted into chloroform. The organic extract was washed with 1 ×HClaq and 1 ×NaCl, dried using MgSO4 and the chloroform removed to leave 5.07 g of a yellow solid. Yield 100%.

1,3 DIACID CHLORIDE (IN SITU)

Diacid (0.80 g, 1.0 mmol) was taken up in dry toluene, thionyl chloride (1.0 ml, 8.4 mmol) was added at room temperature in an inert atmosphere and then the reactants were refluxed for 12 hours. Excess thionyl chloride and toluene were removed by vacuum distillation to leave a brown gum (crude acid chloride). Dry dichloromethane can be used in place of toluene.

1,3 Dipyridyl Derivative

This gum was taken up in dry dichloromethane then added via a cannula to a stirring solution of 4-aminopyridine (0.24 g, 2.4 mmol) and triethylamine (0.19 ml, 2.4 mmol) in dry acetonitrile at room temperature. A brown precipitate was deposited on stirring. This was removed by filtration and the solvents removed to leave 0.83 g of a brown crude product. Recrystallization from dichloromethane: petroleum ether furnished 0.44 g of the cream colored product. Yield 52%.

1,3 Quaternized Dipyridyl Derivative

The 1,3 dipyridyl derivative (0.09 g, 1 mmol) was refluxed in methyliodide (25 ml, excess) for 18 hours. A colour change was observed for the reaction solution from colourless to orange. The methyliodide was removed by distillation to leave 0.12 g of an orange solid. Yield 100%.

EXAMPLE 2

1,3 Ruthenium Bipridyl Complex

The 1,3 dipyridyl derivative of Example 1 (0.20 g, 0.26 mmol) and ruthenium dipryidyl dichloride dihydrate were taken up in ethanol and refluxed for 5 days. Ethanol was removed and the sample was dried under vacuum before the crude reaction mixture was taken up in water and the purple product precipitated out as the $PF_6^-$ salt using ammonium hexafluorophosphate. Yield 25%.

EXAMPLE 3

The diacid chloride of Example 1 was taken up in dichloromethane and added via a cannula to a stirring solution of 4-aminomethylpyridine (0.16 ml, 1.25 mmol) and triethylamine (0.12 ml, 1.25 mmol) in dichloromethane under an inert atmosphere. An immediate colour change was observed from yellow to red and the reactants were stirred for a further 16 hours at room temperature. Solvents were removed to leave a brown crude product which was purified using a silica column (mesh 60–200). Solvents ethyl acetate:ethanol 5:1 Rf 0.16. Yield 20%.

The bis 4-methylaminopyridine derivative so formed (0.1 g) was refluxed in methyl iodide (10 mls, excess) for 16 hours. The excess methyl iodide was removed by distillation to leave the quaternised product as a yellow solid. Yield 100%.

EXAMPLE 4

$^1$H NMR proton titrations were performed on the compounds of Examples 1, 2 and 3. The titrations were carried out using a Bruker 300 MHz spectrometer. The molecular hosts were dissolved in deuteriochloroform and tetrabutylammonium chloride was added to concentrations of 0.25, 0.50, 1.0 and 5.0 mole equivalents and the NMR spectra recorded. The samples were run sequentially in order to keep conditions constant. The change in chemical shift of the NH proton at the recognition site was recorded and plotted against equivalency of chloride. The plots for the compounds of Examples 1 and 2 are shown in FIGS. 1 and 2, respectively, and indicate complex formation in each case. In FIG. 1, the compound of the invention is compared with a model compound in which the pyridine groups are unquaternized.

The titration results for the compound of Example 3 indicated the formation of a 1:1 complex with the chloride ion.

We claim:

1. An ion-sensitive calix(4) arene compound having the formula $A^2+B^{2-}$ wherein A represents a cation capable of forming a receptor-substrate complex with an anion, and B represents sulfate, nitrate or borate, characterized in that the cation is an anion receptor represented by the formula

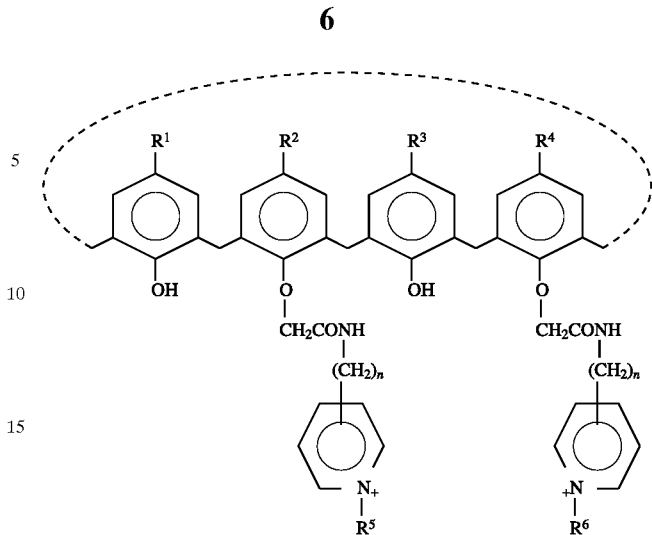

wherein
$R^1$, $R^2$, $R^3$ and $R^4$ are each independently a substituted or unsubstituted alkyl group or a substituted or unsubstituted aryl group wherein substituents are selected from alkyl C(O)NH—, aryl C(O)NH—, alkoxy, aryloxy, alkoxycarbonyl, aryloxycarbonyl, alkylsulfonamido, arylsulfonamido, alkylcarbonyl, alkoxycarbonyl, aryloxycarbonyl, cyano and rnitro;
$R^5$ and $R^6$ are each independently H or a lower alkyl group having from 1 to 4 carbon atoms, or $R^3$ and $R^4$ taken together represent an ethylene bridging group; and
n is 0 or 1.

2. A compound according to claim 1 wherein $R^1$, $R^2$, $R^3$ and $R^4$ are each independently a substituted or unsubstituted alkyl group having from 1 to 20 carbon atoms.

3. A compound according to claim 2 wherein $R^1$, $R^2$, $R^3$ and $R^4$ are each independently a tertiary alkyl group.

4. A compound according to claim 1 wherein $R^1$, $R^2$, $R^3$ and $R^4$ are each independently a substituted or unsubstituted phenyl group.

5. A compound according to claims 1, 2 or 3 wherein $R^3$ and $R^4$ are each methyl groups.

* * * * *